(12) United States Patent
Probst

(10) Patent No.: US 6,440,718 B1
(45) Date of Patent: Aug. 27, 2002

(54) METHOD FOR PRODUCING NON-INFECTIOUS RECOMBINANT PICORNAVIRUS PARTICLES

(75) Inventor: Christian Probst, Lübeck (DE)

(73) Assignee: november Aktiengesellschaft Gesellschaft fur Molekulare Medizin, Erlangen (DE)

( * ) Notice: Subject to any disclaimer, the term of this patent is extended or adjusted under 35 U.S.C. 154(b) by 0 days.

(21) Appl. No.: 09/381,847

(22) PCT Filed: Mar. 26, 1998

(86) PCT No.: PCT/DE98/00879

§ 371 (c)(1),
(2), (4) Date: Dec. 17, 1999

(87) PCT Pub. No.: WO98/44122

PCT Pub. Date: Oct. 8, 1998

(30) Foreign Application Priority Data

Mar. 27, 1997 (DE) .......................................... 197 12 899

(51) Int. Cl.[7] ................................................. C12N 7/00
(52) U.S. Cl. ........................... 435/235.1; 424/204.1; 424/226.1; 435/69.1; 435/70.1; 435/91.1; 435/91.33; 435/183; 435/239; 435/240.2; 435/252.3; 435/320.1; 435/465
(58) Field of Search ........................... 424/204.1, 226.1; 435/69.1, 70.1, 91.1, 91.33, 183, 235.1, 239, 240.2, 252.3, 465; 536/23.72; 935/22, 23, 32

(56) References Cited

U.S. PATENT DOCUMENTS 5,294,548 A * 3/1994 McLinden et al. ........ 435/235.1

FOREIGN PATENT DOCUMENTS

WO     WO 93/01279     1/1993

OTHER PUBLICATIONS

Ansardi et al. Complementation of a poliovirus defective genome by a recombinant vaccinia virus which provides poliovirus P1 capsid precurser in trans. Journal of Virology (1993) vol. 67, pp. 3684–3690.*

Ansardi et al. Coinfection with recombinant vaccinia viruses expressing poliovirus P1 and P3 proteins results in polyprotein processing and formation of empty capsid structures. Journal of Virology (1991) vol. 65, No. 2, pp. 2088–2092.*

Schultheiss T., et al., Cleavage Specificity of Purified Recombinant Hepatitis A Virus 3C Proteinase on Natural Substrates,: *J. Virology*, vol. 69, No. 3, pp. 1727–1733 (1995).

Emerson, S., et al., "2B and 2C Mutations are Essential but Mutations throughout the Genome of HAV Contribute to Adaption to Cell Culture," *Virology*, vol. 194, pp. 475–480 (1993).

Probst C., et al., "Proteinase 3C–Mediated Processing of VP1–2A of Two Hepatitis A Virus Strains: In Vivo Evidence for Cleavage at Amino Acid Position 273/274 of VP1," *J. Virology*, vol. 71, No. 4, pp. 3288–3292 (1997).

* cited by examiner

*Primary Examiner*—Jeffrey Stucker
*Assistant Examiner*—Ulrike Winkler
(74) *Attorney, Agent, or Firm*—Fish & Richardson P.C., P.A.

(57) ABSTRACT

The invention relates to a process for recombinantly preparing picornavirus particles, in particular hepatitis A virus particles, their precursors and particles which are derived therefrom, with a structural protein precursor molecule (P1-2A or P1) and the corresponding P3 region (3ABCD) being coexpressed in cis or in trans.

16 Claims, 4 Drawing Sheets

SFV1-HM-P3 + SFV3-HM/HM-P1-2A(E/S)

HAAg (relative Einheiten) vs Saccharose (% w/w), peak near 20%, range 30 to lower.

FIG. 4A pGEM2-HAV-Δ2BC

HAAg (relative Einheiten) vs Saccharose (% w/w), peak near 20%, range 30 to lower.

FIG. 4B

SEQUENCE LISTING

<160> NUMBER OF SEQ ID NOS: 4

<210> SEQ ID NO 1
<211> LENGTH: 44
<212> TYPE: DNA
<213> ORGANISM: Artificial Sequence
<220> FEATURE:
<223> OTHER INFORMATION: primer

<400> SEQUENCE: 1
atggtccgga gcaccatggg aatttcagat gatgataatg atag    44

<210> SEQ ID NO 2
<211> LENGTH: 40
<212> TYPE: DNA
<213> ORGANISM: Artificial Sequence
<220> FEATURE:
<223> OTHER INFORMATION: primer

<400> SEQUENCE: 2
tttagctagc tcatgaaagg tcacaaatga aacactggtc    40

<210> SEQ ID NO 3
<211> LENGTH: 39
<212> TYPE: DNA
<213> ORGANISM: Artificial Sequence
<220> FEATURE:
<223> OTHER INFORMATION: primer

<400> SEQUENCE: 3
ggggtaccca caaccatggt tggagatgat tctggaggt    39

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
ccggtaccct cagtataaaa gaaagaaatt taggc    35

METHOD FOR PRODUCING NON-INFECTIOUS RECOMBINANT PICORNAVIRUS PARTICLES

This application claims benefit of PCT/DE98/00879, filed Mar. 26, 1998, now abandoned, which claims benefit of DE 197 12 899.8, filed Mar. 27, 1997, which issued as German Patent No. 197 12 899 on Dec. 10, 1998.

The invention relates to a process for recombinantly preparing picornavirus particles, in particular hepatitis A virus particles, their precursors and particles which are derived therefrom.

It is known from the state of the art to prepare picornavirus strains by culturing in eukaryotic cells. Such culturing is particularly inefficient in the case of particular members of the Picornaviridae family, for example the hepatitis A virus. A further disadvantage is that the picornaviruses which are cultured in the eukaryotic cells are infectious. They have to be chemically inactivated before being used, for example as a dead vaccine. Residues of the substance used for the inactivation, for example formaldehyde, may elicit allergic reactions and alter the antigenicity of the virus particle.

Stapelton, J. T. et al. 1990 have described (in Hollinger, F. B. et al.: Viral hepatitis and liver disease, 50–54) a more efficient method which can be used, in particular, for preparing empty, recombinant hepatitis A virus particles. The particle yields which are achieved by this method are likewise not adequate for commercial applications.

It is furthermore known from the state of the art that polyprotein processing is mediated by 3CD, 3C and 2A in the case of the enterovirus and rhinovirus genera, by L-proteinase and 3C in the case of the cardiovirus and apthovirus genera, and by 3C in the case of the hepatovirus genus. It is not known from the state of the art whether other nonstructural proteins are involved in the formation of empty virus particles.

The object of the present invention is to specify a process which eliminates the disadvantages of the state of the art. The aim is, in particular, to make available a more efficient process.

According to the invention, a structural protein precursor molecule and the corresponding P3 region (3ABCD) are coexpressed, in cis or in trans, for the purpose of recombinantly preparing picornavirus particles, in particular hepatitis A virus particles, their precursors and particles which are derived therefrom. The part proteins 2B and 2C are advantageously not expressed in this connection. One of the advantages of the novel process is that the inhibitory effects associated with expressing the part proteins 2B and 2C are eliminated and use is only made of the minimum sequences which are required for efficiently synthesizing empty picornavirus particles. This improves the efficiency of the process, on the one hand, and excludes the possibility of picornaviral replication, on the other hand. Using the complete P3 region markedly increases the efficiency of the synthesis of empty picornavirus particles, or their precursor molecules, as compared with only using the 3C and/or 3CD proteinases.

Advantageously, the structural protein precursor molecule possesses sequences encoding P1 or P1-2A. The P1 structural protein precursor molecule is in particular used in the case of the enterovirus and rhinovirus genera. In the case of the cardiovirus, aphthovirus and hepatovirus genera, use is preferably made of the structural protein precursor molecule which possesses the sequence encoding P1-2A.

A particularly efficient preparation of empty hepatitis A virus particles can be achieved when the VP1-2A cleavage site at amino acid position 273/274 is occupied by a glutamate/serine pair or a glutamine/serine pair, with the indication of the amino acid position relating to the sequence of the attenuated strain HM175 (in accordance with Cohen, J. I. et al. 1987, Journal of Virology 61:3035–3039).

When the structural protein precursor molecule and the P3 proteins are expressed in cis, there is equimolar expression of the two genome regions. This enables empty hepatitis A virus particles to be prepared efficiently. An even more efficient preparation of hepatitis A virus particles can be achieved by optimizing the molar ratio of the structural protein precursor molecule and the P3 proteins by means of expressing in trans. The coexpression in trans can be carried out by coexpressing the structural protein precursor molecule and the P3 region when they are encoded on separate vectors. This coexpression can also be carried out using a bicistronic expression vector or a bicistronic mRNA. In this context, at least two promoter sequences or translation initiation sequences which are of differing efficiencies are advantageously located in front of the P3 cistron and the structural protein cistron. This makes it possible to adjust the molar ratio of the structural protein precursor molecule and the corresponding P3 region optimally for achieving efficient synthesis of empty picornavirus particles.

It has proved to be advantageous for the expression of the proteins of the P3 region to be controlled negatively in cis by means of cloning sequence elements of the 5' non-translated region (=5' NTR) in front of the sequences encoding the P3 region. The negative control of the expression of the proteins of the P3 region contributes, when this region is being coexpressed together with the structural protein precursor molecule, to the two components being expressed in an optimal ratio.

The negatively controlling sequence elements employed can expediently be the sequences which are located in front of the internal ribosome binding site of the 5' NTR. Particularly in the case of the hepatitis A virus, it has proved to be advantageous for the sequence elements of the 5' NTR to be the 24 or 45 5' terminal nucleotides of the 5' NTR of the hepatitis A virus genome, or to be derived therefrom.

According to another organizational feature of the process, the coexpression is carried out in eukaryotic or prokaryotic cells or in the corresponding cell extracts, with the sequences which are to be coexpressed being cloned 3' of a eukaryotic or of a prokaryotic promoter. The Semliki forest virus expression system (Liljeström P., Garoff H., Bio/Technology 9, 1356–1361) or the baculovirus expression system (Bishop D H L, 1990, 62–67, Current Opinion in Biotechnology) can, for example, be used in this context.

The invention furthermore encompasses a kit or a combination of means for carrying out the above-described process. Finally, the picornavirus particles according to the invention can be used for preparing a medicament or vaccine or for preparing galenics or diagnostic agents.

The invention is explained in more detail below in the drawing and with the aid of implementation examples.

Figure 1:
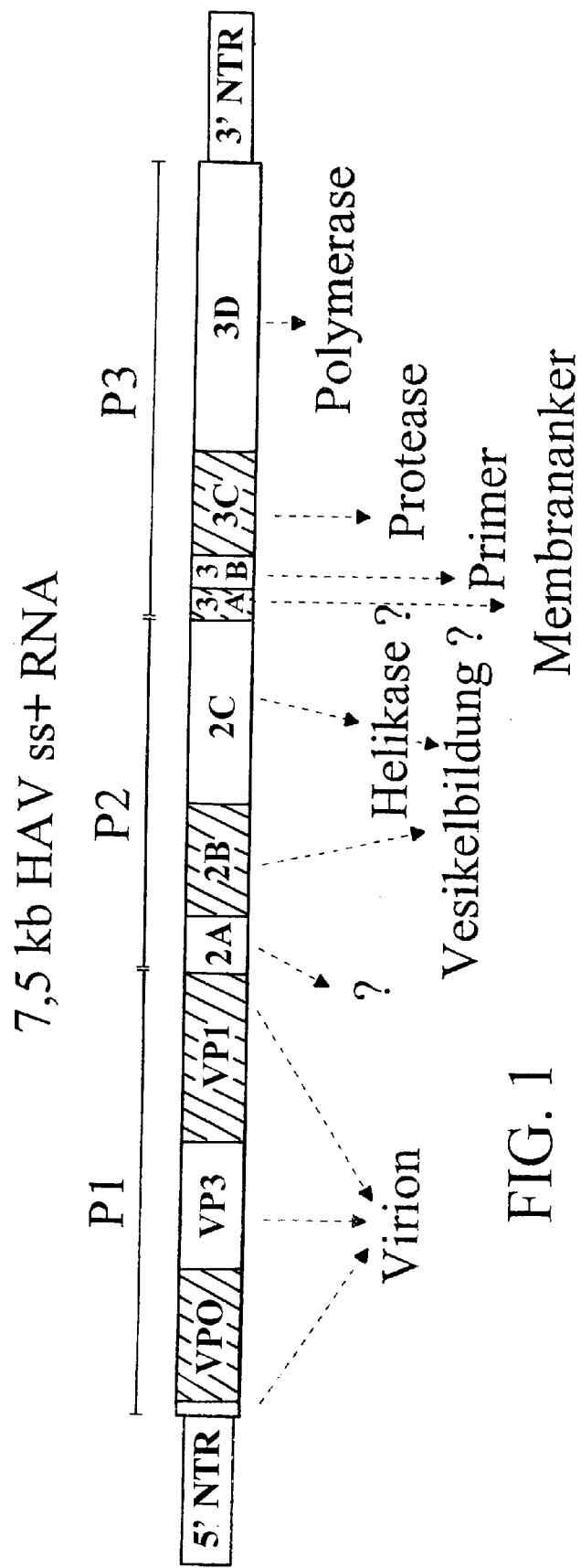
FIG. 1 shows the genomic organization of the hepatitis A virus.

FIG. 1 depicts the genomic organization of the hepatitis A virus. The internal ribosome binding site (IRES) which is located in the 5' non-translated region (5' NTR) mediates the initiation of polyprotein synthesis. The polyprotein encodes the structural proteins (VP4–VP1) and the nonstructural proteins (2A–3D). The former form the virus coat; the latter assume various functions in the lifecycle of the virus.

Figure 2:
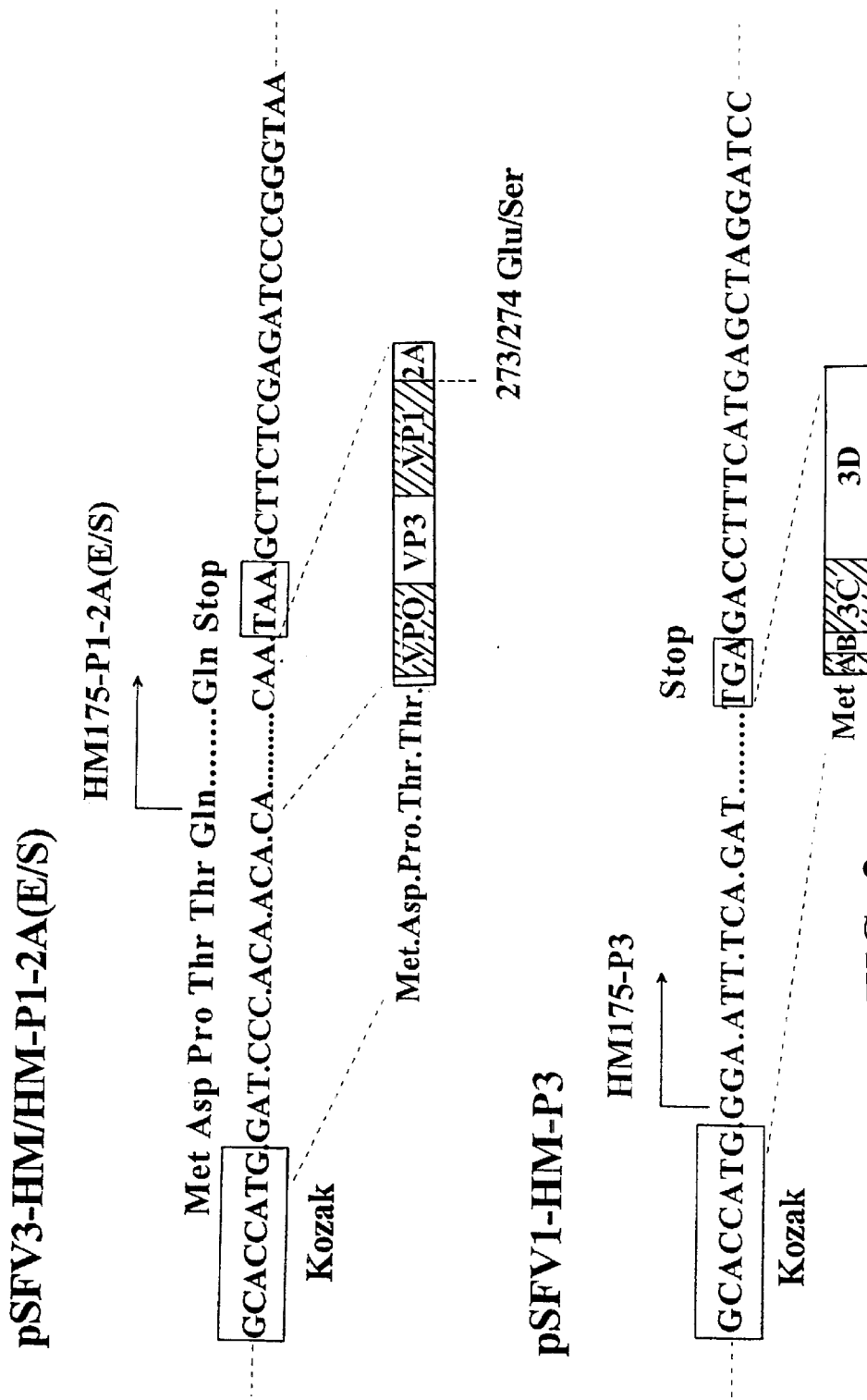
FIG. 2 shows the Semliki forest virus expression constructs pSFV3-HM/HM-P1-2A(E/S) and pSFV1-HM-P3.

FIG. 2 shows pSFV3-HM/HM-P1-2A(E/S), which encodes the P1-2A structural protein precursor molecule having a Glu/Ser-VP1-2A cleavage site, and pSFV1-HM-P3, which encodes the complete P3 region of the attenuated HAV strain HM175. After transfecting in-vitro transcribed and capped RNA into suitable host cells, the P3 proteins mediate their own proteolytic processing and the proteolytic processing of the P1-2A structural protein precursor molecule. In addition to this, they mediate the efficient formation of empty hepatitis A virus particles.

Figure 3:
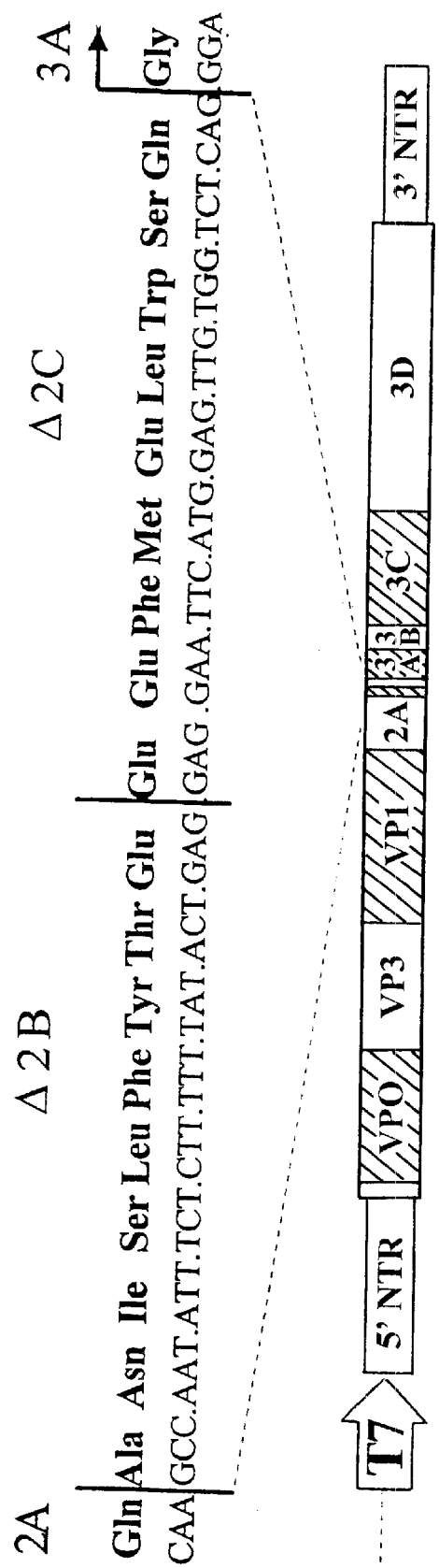
FIG. 3 shows the expression construct pGEM2-HAV-Δ2BC, and FIGS. 4a and b show the detection of empty, recombinantly produced hepatitis A virus particles.

The expression construct possessing a T7 promoter, which is depicted in FIG. 3, encodes an HAV polyprotein from which the 2BC region has been almost completely deleted. The reading frame of the part polyprotein has not been destroyed. After transfecting into suitable cells and making available T7 RNA polymerase, the T7 promoter mediates the transcription of the partially deleted viral genome. The remains of the 2BC region make possible the 3C-mediated polyprotein cleavage between 2A and Δ2B and also between Δ2C and 3A and consequently the preparation of authentic P1-2A and P3. The P3 proteins mediate the subsequent proteolytical cleavages of the recombinant proteins and enable empty hepatitis A virus particles to be formed efficiently.

FIGS. 4a and 4b depict the profiles of the sucrose gradients of the constructs shown in FIG. 2 and FIG. 3 after ultracentrifugation. The viral antigen was detected in an ELISA using the neutralizing monoclonal antibody K2-4F2. The major portion of the K2-4F2-reactive viral antigen migrated into the 20% (w/w) sucrose fraction. This gives a sedimentation constant of about 90S. Consequently, the recombinantly produced hepatitis A virus antigen corresponds structurally and immunologically to empty hepatitis A virus particles.

The following parameters were used in the ultracentrifugation: running time=75 minutes; centrifuge speed=48,000 rpm; temperature=5° C.; rotor SW65 (Beckmann); gradient composition: 5–30%(w/w) sucrose in 10 mM tris, pH 7.3. The gradient was calibrated using an HAV-infected cell extract.

EXAMPLES

1. The Production of Empty Hepatitis A Virus Particles by Coexpressing P1-2A and P3 in Trans Using the Semliki Forest Virus Expression System (Liljeström, P., Garoff, H., Bio/Technology 9, 1356–1361).

The 2.7 kb MscI/XhoI fragment from pEXT7-HM/HM-P1-2A(E/S) and the vector pSFV3 (Gibco-BRL, Bethesda, USA), which was linearized with BamHI and dephosphorylated, were used for cloning pSFV3-HM/HM-P1-2A(E/S) as depicted in FIG. 2. The single-stranded protruding ends were removed, prior to the ligation, by means of a Klenow filling-in reaction. The plasmid pSFV3-HM/HM-P1-2A(E/S) encodes the P1-2A of the (attenuated) HAV strain HM175, together with 5 N-terminal foreign amino acids, with the VP1-2A cleavage site at the VP1 amino acid position 273/274 being a glutamate/serine pair (E/S). Translation initiation takes place, in a cap-dependent manner, by way of a start codon which is located in a Kozak consensus sequence (Kozak, M. 1989. J. Cell. Biol. 108:229–225).

For cloning pSFV1-HM-P3 (see FIG. 2), pSFV1 (Gibco-BRL, Bethesda, USA) was first of all linearized with BamHI and the single-stranded protruding ends were filled in by means of a Klenow polymerase reaction. The P3 genomic region (bases 4996–7409) was amplified by PCR using the "P3 sense" (5'- ATG GTC CGG AGC ACC ATG GGA ATT TCA GAT GAT GAT AAT GAT AG-3'SEQ ID NO. 3.) and "P3 antisense" (5'-T TTA GCT AGC TCA TGA AAG GTC ACA AAT GAA ACA CTG GTC A-3') primers and pT7-HAV1 as the template. The PCR fragment was then cut with Kpn21/NHeI, after which the protruding single-stranded regions were filled in using Klenow polymerase. pSFV1-HM-P3 was cloned by inserting this fragment into the dephosphorylated pSFV1 vector fragment. pSFV1-HM-P3 encodes the entire P3 region of the attenuated HAV strain HM175, with a methionine residue being encoded as an additional N-terminal amino acid. Translation initiation is mediated by a Kozak translation initiation sequence.

The SpeI-linearized plasmids pSFV3-HM/HM-P1-2A(E/S) and pSFV1-HM-P3 are used as the templates for the in-vitro transcription of capped RNA (Current Protocols in Molecular Biology, Supplement 25, John Wiley & Sons, Inc.). Equal quantities of the unpurified SFV3-HM/HM-P1-2A(E/S) and SFV1-HM-P3 in-vitro transcription mixtures are mixed together and in each case transfected by electroporation into $2\times10^6$ COS7 cells (for transfection parameters, see Wilk, T. et al. 1992, Virus Genes 6:229–246). The cells are then sown on 30 cm$^2$ cell culture dishes and incubated in a cell culture incubator for 48 hours. The recombinantly produced empty virus particles are detected, for example, by ultracentrifuging in a continuous 5–30%(w/w) sucrose gradiant. For this, the fractions of the sucrose gradient are analyzed by an "enzyme-linked immunosorbent assay" (ELISA) which is based on the neutralizing monoclonal antibody K2-4F2 (MacGregor, A. W. et al. 1983, J. Clin. Microbiology 18: 1237–1243). The recombinantly produced antigen possesses a sedimentation constant of about 90S and, as is evident from FIG. 4a, corresponds structurally and immunologically to empty hepatitis A virus particles.

2. Production of Empty Hepatitis A Virus Particles by Coexpressing P1-2A and P3 in cis in the vaccinia T7 Expression System (Fuerst, T. R. et al. 1986, Proc. Natl. Acad. Sci. USA. 83:8122–8126).

The sequence region of the plasmid p5'P2P3-3'.18f (Zhang, H. et al. 1995, virology 212:686–697) which encodes the HAV genome of an attenuated HAV strain is first of all placed under the control of a T7 promoter. To do this, the 7.5 kb HindIII/SphI fragment is inserted into pGEM2 which has been cut in a compatible manner.

After that, the 2BC genome region is deleted from the resulting cDNA construct pGEM2-HAV. For this, the VP1-Δ2B-encoding region is amplified by PCR using the "VP1 sense" (5'-GGG GTA CCC ACA ACC ATG GTT GGA GAT GAT TCT GGA GGT-3'SEQ ID NO. 3) and "Δ2B antisense" (5'-CC GGT ACC CTC AGT ATA AAA GAA AGA AAT TTA GGC-3'SEQ ID NO. 2) primers and pGEM2-HAV as the template. The resulting DNA fragment is cut with KpnI and the single-stranded protruding end is digested off by means of a mung bean nuclease reaction; the fragment is then cut with SacI. This fragment is ligated into pGEM2-HAV which has been cut with EcoRI/SacI SacI and whose EcoRI cleavage site has been filled in using Klenow polymerase. The resulting construct, pGEM2-HAV-Δ2BC (FIG. 3), is transfected into COS7 cells by means of lipofection. Expression is initiated by infecting with vaccinia T1 virus. 24 hours after the infection, the cell extract is analyzed in an analogous manner to that described in Example 1. The recombinantly produced antigen has a sedimentation constant of 90S and, as is evident from FIG. 4b, corresponds structurally and immunologically to empty hepatitis A virus particles.

What is claimed is:

1. A method for recombinantly producing non-infectious Hepatitis A virus particles comprising expressing a nucleic acid encoding a Hepatitis A virus structural protein precursor molecule and a nucleic acid encoding a Hepatitis A virus P3 region in a cell, wherein said cell does not express Hepatitis A virus proteins 2B and 2C.

2. The method of claim 1, wherein said nucleic acids are expressed in cis orientation.

3. The method of claim 1, wherein said nucleic acids are expressed in trans orientation.

4. The method of claim 3, wherein said nucleic acids are expressed from a bicistronic expression vector.

5. The method of claim 1, wherein said cell is eukaryotic.

6. The method of claim 1, wherein said structural protein precursor molecule is P1.

7. The method of claim 1, wherein said structural protein precursor molecule is P1-2A.

8. The method of claim 1, wherein positions 273 and 274 of P1-2A are glutamine and serine, respectively.

9. The method of claim 1, wherein positions 273 and 274 of P1-2A are glutamate and serine, respectively.

10. The method of claim 1, wherein said nucleic acid encoding said P3 region comprises negative control elements.

11. The method of claim 10, wherein said negative control elements comprise 5' terminal nucleotides of the 5' non-translated region of said P3 region.

12. The method of claim 1, wherein said nucleic acids comprise a promoter.

13. The method of claim 12, wherein said promoter is a CMV promoter.

14. The method of claim 12, wherein said promoter is a T7 promoter.

15. The method of claim 1, wherein said P3 region encodes 3A, 3B, 3C, and 3D.

16. A kit for producing recombinant non-infectious Hepatitis A virus particles, said kit comprising:
   a) a nucleic acid encoding a Hepatitis A virus structural protein precursor molecule; and
   b) a nucleic acid encoding a Hepatitis A virus P3 region.

* * * * *